United States Patent
Kelly et al.

(10) Patent No.: US 11,125,658 B2
(45) Date of Patent: Sep. 21, 2021

(54) FLUID SAMPLING UNIT

(71) Applicant: Blue-Water Management Solutions, Inc., Port Sanilac, MI (US)

(72) Inventors: Daniel T. Kelly, Port Sanilac, MI (US); Christine B. Kelly, Port Sanilac, MI (US)

(73) Assignee: BLUE-WATER MANAGEMENT SOLUTIONS, INC., Port Sanilac, MI (US)

( * ) Notice: Subject to any disclaimer, the term of this patent is extended or adjusted under 35 U.S.C. 154(b) by 97 days.

(21) Appl. No.: 16/715,257

(22) Filed: Dec. 16, 2019

(65) Prior Publication Data
US 2020/0200652 A1 Jun. 25, 2020

Related U.S. Application Data

(60) Provisional application No. 62/781,645, filed on Dec. 19, 2018.

(51) Int. Cl.
*G01N 1/20* (2006.01)
*G01N 33/18* (2006.01)
*G01N 29/44* (2006.01)

(52) U.S. Cl.
CPC ....... *G01N 1/2035* (2013.01); *G01N 29/4472* (2013.01); *G01N 33/18* (2013.01); *G01N 2001/205* (2013.01); *G01N 2203/0246* (2013.01)

(58) Field of Classification Search
CPC ........... G01N 1/2035; G01N 2001/205; G01N 33/18; G01N 1/02; G01N 1/10; G01N 1/2226; G01N 30/20; G01N 2203/0246; G01N 29/4472
See application file for complete search history.

(56) References Cited

U.S. PATENT DOCUMENTS

| | | | |
|---|---|---|---|
| 6,035,704 A | 3/2000 | Newman | |
| 6,635,172 B2 | 10/2003 | Newman | |
| 7,104,115 B2 | 9/2006 | Kahn et al. | |
| 7,434,781 B2 | 10/2008 | Taylor et al. | |
| 8,043,094 B2 * | 10/2011 | Bahler | G09B 25/025 434/276 |
| 8,531,303 B2 | 9/2013 | Pham et al. | |

(Continued)

FOREIGN PATENT DOCUMENTS

| | | |
|---|---|---|
| CN | 102297932 A | 12/2011 |
| CN | 104316665 A | 1/2015 |

*Primary Examiner* — John Fitzgerald
*Assistant Examiner* — Truong D Phan
(74) *Attorney, Agent, or Firm* — Brooks Kushman P.C.

(57) ABSTRACT

A fluid sampling unit includes a housing and a shutoff valve adapted to selectively permit and restrict fluid flow to a fluid line disposed within an internal cavity of the housing. An electrically-actuated valve is disposed within the housing downstream from, and in fluid communication with, the shutoff valve. A first metallic line including copper is disposed within the housing in fluid communication with and between the shutoff valve and the electrically-actuated valve. A second metallic line including lead is disposed within the housing in fluid communication with and between the shutoff valve and the electrically-actuated valve. A control unit includes a controller adapted to selectively actuate the electrically-actuated valve.

20 Claims, 4 Drawing Sheets

(56) References Cited

U.S. PATENT DOCUMENTS

| | | |
|---|---|---|
| 9,151,023 B2 | 10/2015 | Taylor et al. |
| 2009/0123340 A1* | 5/2009 | Knudsen ................ G08B 21/12 |
| | | 422/105 |

* cited by examiner

FLUID SAMPLING UNIT

CROSS REFERENCE TO RELATED APPLICATIONS

This application claims the benefit of U.S. Provisional Application Ser. No. 62/781,645 filed Dec. 19, 2018, the disclosure of which is hereby incorporated in its entirety by reference herein.

TECHNICAL FIELD

This disclosure relates to a fluid sampling unit, and more particularly, to a self-contained, programmable fluid sampling unit.

BACKGROUND

Drinking water regulations, such as those established by the Environmental Protection Agency or state agencies, often require municipalities and other entities to test drinking water. Drinking water may be tested for corrosivity and contents such as lead and copper that may be present in the water from the piping system through which the water is distributed.

In many instances, the regulations require that community water supplies identify a pool of lead and copper sampling sites large enough to ensure a sufficient number of sites are available for sampling based on a distribution system materials evaluation. Regulations may further require that samples be collected from "Tier 1" sites unless certain criteria exist. Tier 1 sites may include single family residence with (i) lead service lines, (ii) copper plumbing with lead solder installed after 1982 and before 1989, or (iii) interior lead plumbing. A service line may be defined as a pipe that runs from a water main, including corporation stops and curb stops, to customer site piping or to a building (e.g., to the first shut off valve inside the building, or to five feet inside the building, whichever is shorter).

If a water system has lead service lines (LSL), regulations may require that at least 50 percent of the sampling sites must have an LSL. EPA regulations may require that sites with lead goosenecks or pigtails (commonly defined as the publicly-owned portion of the service line between the water main and a either a connector line or the curb box) be considered Tier 1 sites.

The monitoring of lead and other contaminants in tap water may be done using sampling protocols. Sampling protocols are intended to measure the lead levels in drinking water to assess the effectiveness of corrosion control treatment employed by public water systems to minimize lead in drinking water. Sampling protocols often seek to capture worst-case lead-in-water levels in highest-risk homes to enable a system-wide assessment of the efficacy of corrosion control treatment while complying with various other treatment or water quality objectives.

Public water systems often rely upon volunteer residents to perform drinking water sampling. While public water systems may issue required sampling protocols to volunteer residents, the actual procedures used to collect a sample may not always be known or confirmable by public water systems with a sufficient degree of certainty.

SUMMARY

In at least one approach, a fluid sampling unit is provided. The fluid sampling unit may include a housing, and a shutoff valve adapted to selectively permit and restrict fluid flow to a fluid line disposed within an internal cavity of the housing. The fluid sampling unit may further include an electrically-actuated valve disposed within the housing downstream from, and in fluid communication with, the shutoff valve. The fluid sampling unit may further include a first metallic line including copper. The first metallic line may be disposed within the housing in fluid communication with and between the shutoff valve and the electrically-actuated valve. The fluid sampling unit may further include a second metallic line including lead. The second metallic line may be disposed within the housing in fluid communication with and between the shutoff valve and the electrically-actuated valve. In at least one approach, at least one of the first metallic line and the second metallic line may be a coiled metallic line. Additional lines of other materials such as steel or plastic can optionally be included.

The fluid sampling unit may further include a control unit. The control unit may include a controller adapted to selectively actuate the electrically-actuated valve to at least partially open the electrically-actuated valve in response to the fluid flow being maintained within the first and second metallic lines for a programmed period of time. In at least one approach, the programmed period of time may be at least six hours.

The fluid sampling unit may further include a dispenser disposed within the housing downstream from the electrically-actuated valve. The fluid sampling unit may further include a receptacle basin disposed within the housing and gravitationally below the dispenser to receive the fluid flow from the dispenser. The dispenser may be spaced vertically above the receptacle basin such that the sampling unit defines an airgap between the dispenser and the receptacle basin. The fluid sampling unit may further include a sample receptacle that may be removably received within the receptacle basin to receive the fluid flow from the dispenser.

In at least one approach, the fluid sampling unit may further include a fluid outlet that may be in fluid communication with the receptacle basin, and a check valve that may be disposed fluidly disposed between the receptacle basin and the fluid outlet.

The fluid sampling unit may further include a removable cover securable to the housing to selectively permit and restrict access to the internal cavity of the housing.

In at least one approach, the fluid sampling unit may further include a turbine that may be disposed within the housing in fluid communication with and between the shutoff valve and the electrically-actuated valve. The fluid sampling unit may further include a battery in electrical communication with the turbine. In at least one approach, the battery may be in electrical communication with the electrically-actuated valve.

The fluid sampling unit may further include a flow meter that may be disposed within the housing and in fluid communication with the electrically-actuated valve. The controller may be adapted to selectively actuate the electrically-actuated valve to at least partially close the electrically-actuated valve in response to a programmed volume of the fluid flow flowing through the flow meter.

In at least one approach, the fluid sampling unit may further include a communication device that may include a communication interface adapted to receive, send, or both receive and send wireless communications.

The fluid sampling unit may further include a backflow preventer that may be disposed fluidly between the shutoff valve and the electrically-actuated valve to prevent backflow of the fluid flow through the shutoff valve.

In at least one approach, a method for sampling fluid includes fluidly connecting a fluid sampling unit to a service line of a public water system that includes a plurality of service lines. The fluid sampling unit may include a housing having an electrically-actuated valve, a first metallic line including copper, and a second metallic line including lead disposed within an internal cavity of the housing.

The method may include, via a controller, successively opening and closing the electrically-actuated valve for a first programmed period of time. The method may further include, subsequent to expiration of the first programmed period of time, maintaining the electrically-actuated valve in a closed configuration for a second programmed period of time to maintain a fluid volume within the first and second metallic lines. The programmed period of time may be, for example, at least six hours, however longer of shorted periods may be selected.

The method may further include, subsequent to expiration of the second programmed period of time and during a third programmed period of time, at least partially opening the electrically-actuated valve responsive to a sampling request to discharge the fluid volume.

In at least one approach, at least partially opening the electrically-actuated valve may communicate the fluid flow to a removable sample receptacle disposed within the internal cavity of the housing. The method may further include, via the controller, at least partially opening the electrically-actuated valve responsive to an expiration of the third programmed period of time.

In at least one approach, the method may further include removing a cover that is removably secured the housing, and removing the removable sample receptacle, including a fluid sample within the removable sample receptacle, from the housing. The method may further include sampling the fluid sample to determine at least one of a lead content level and a copper content level within the fluid sample.

In at least one approach, the fluid sampling unit may be a portable, self-contained fluid sampling unit.

DETAILED DESCRIPTION

Embodiments of the present disclosure are described herein. It is to be understood, however, that the disclosed embodiments are merely examples and other embodiments may take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the present invention. As those of ordinary skill in the art will understand, various features illustrated and described with reference to any one of the figures may be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Figure 1:
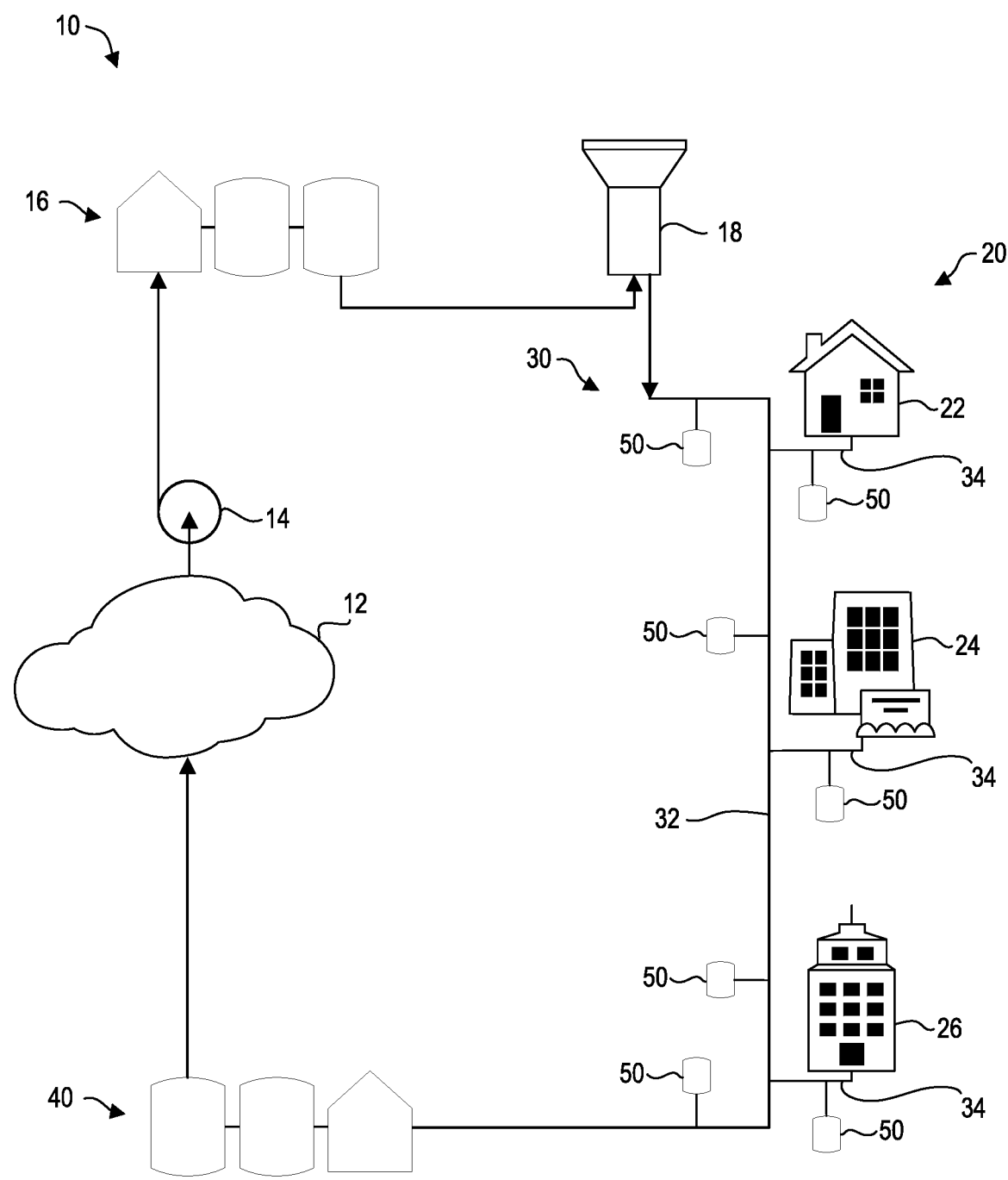
FIG. 1 is a schematic representation of an example public water distribution network.

Referring now to FIG. 1, a water system or distribution network 10 may provide water for human consumption through pipes or other constructed conveyances. The water distribution network 10 may be a public water distribution network. As used herein, a "public water" system or distribution network refers to end consumers. As such, the water distribution network 10 may be publicly or privately owned.

The water distribution network 10 may include a water source 12. The water source 12 may include one or more of a surface water source, a ground water source, or other water source. A surface water source may include one or more of a stream, river, lake, reservoir, ocean, etc. Water from a ground water source may accessed, for example, through a well.

Water may be drawn from the water source 12, for example, using one or more pumps 14. Prior to or after pumping, the water may be passed through one or more screens to remove debris.

The water may be pumped to a water treatment facility 16. As drinking water sources may be subject to contamination and may require appropriate treatment to remove disease-causing agents, various operations may be performed on the water while the water is at the water treatment facility 16. As such, public drinking water systems may use various methods of water treatment to provide safe drinking water for their communities. Example steps that may be performed at the water treatment facility may include at least one of coagulation and flocculation, sedimentation, filtration, and disinfection.

Coagulation and flocculation are often the first steps in water treatment. Chemicals with a positive charge are added to the water. The positive charge of these chemicals neutralizes the negative charge of dirt and other dissolved particles in the water. When this occurs, the particles bind with the chemicals and form larger particles called floc. During sedimentation, floc settles to the bottom of the water supply, due to its weight. Once the floc has settled to the bottom of the water supply, during filtration, the clear water on top passes through filters of varying compositions (sand, gravel, and charcoal) and pore sizes, in order to remove dissolved particles such as dust, parasites, bacteria, viruses, and chemicals. After the water has been filtered, a disinfectant (for example, chlorine, chloramine) may be added in order to kill any remaining parasites, bacteria, and viruses, and to protect the water from germs when it is piped to homes and businesses.

From the water treatment facility 16, treated water may be transported to a water tower 18 or other elevated structure that supports a water tank. The water tower 18 may be constructed at a height sufficient to pressurize a water supply system for the distribution of potable water, and to provide emergency storage for fire protection.

One or more service locations 20 may be connected to a water source, such as a water tower 18, to receive water from the water source. The service locations 20 may include one or more of single family residences 22, multi-family residences 24, and public or commercial buildings 26.

The service locations 20 may be connected to a water source through a water distribution network 30. The water distribution network 30 may include one or more water mains 32 that may be connected to the water source (e.g., water tower 18) to receive water from the water source. The service locations 20 may be connected to water mains 32 via one or service lines 34. The service lines 34 may include pigtail, gooseneck or other fittings to connect a water main 32 to a building inlet of a single family residence 22, multi-family residence 24, or public or commercial building 26.

A water distribution network 30 may be connected to a wastewater treatment facility 40. Wastewater may be treated at a wastewater treatment facility 40 clean wastewater for discharge into streams or other receiving waters, or for reuse. Example processes performed at a wastewater treatment facility 40 may include phase separation (wherein impurities may be transferred into a non-aqueous phase), sedimentation (wherein solids and non-polar liquids may be removed from wastewater by gravity, for example, when density differences are sufficient to overcome dispersion by turbulence), filtration (wherein colloidal suspensions of fine solids may be removed by filtration through fine physical barriers), oxidation (wherein the biochemical oxygen demand of wastewater and the toxicity of some impurities may be reduced), biochemical oxidation (wherein organic compounds useful as a food supply for the treatment ecosystem may be removed), chemical oxidation (wherein some persistent organic pollutants and concentrations remaining after biochemical oxidation may be removed), and polishing. These processes may be performed as single- or multi-stage processes. For example, in a primary stage, solids may be allowed to settle and may be removed from wastewater. As sewage enters a wastewater treatment facility 40 for treatment, it may flow through a screen, which removes large floating objects, and into a grit chamber, where cinders, sand, and small stones may settle to the bottom. Solids can be removed from sewage in a sedimentation tank. A secondary stage may use biological processes to further purify wastewater. The secondary stage of treatment may remove organic matter in sewage.

Water treated at the wastewater treatment facility 40 may be returned to a stream, river, lake, reservoir, ocean, etc. (for example, water source 12), or may be reused.

One or more sampling units 50 may be provided along the water distribution network 30. A sampling unit 50 may be provided between a water source (e.g., water tower 18) and a first service location 20, between service locations 20, and/or between a service location 20 and a wastewater treatment facility 40. The sampling units 50 may be fluidly connected to a water main 32 and/or to a service line 34 that connects a service location 20 to a water main 32. The sampling unit 50 maybe located in-ground adjacent to the building as shown in FIG. 1 or located inside the building in a basement or utility room.

Figure 2:
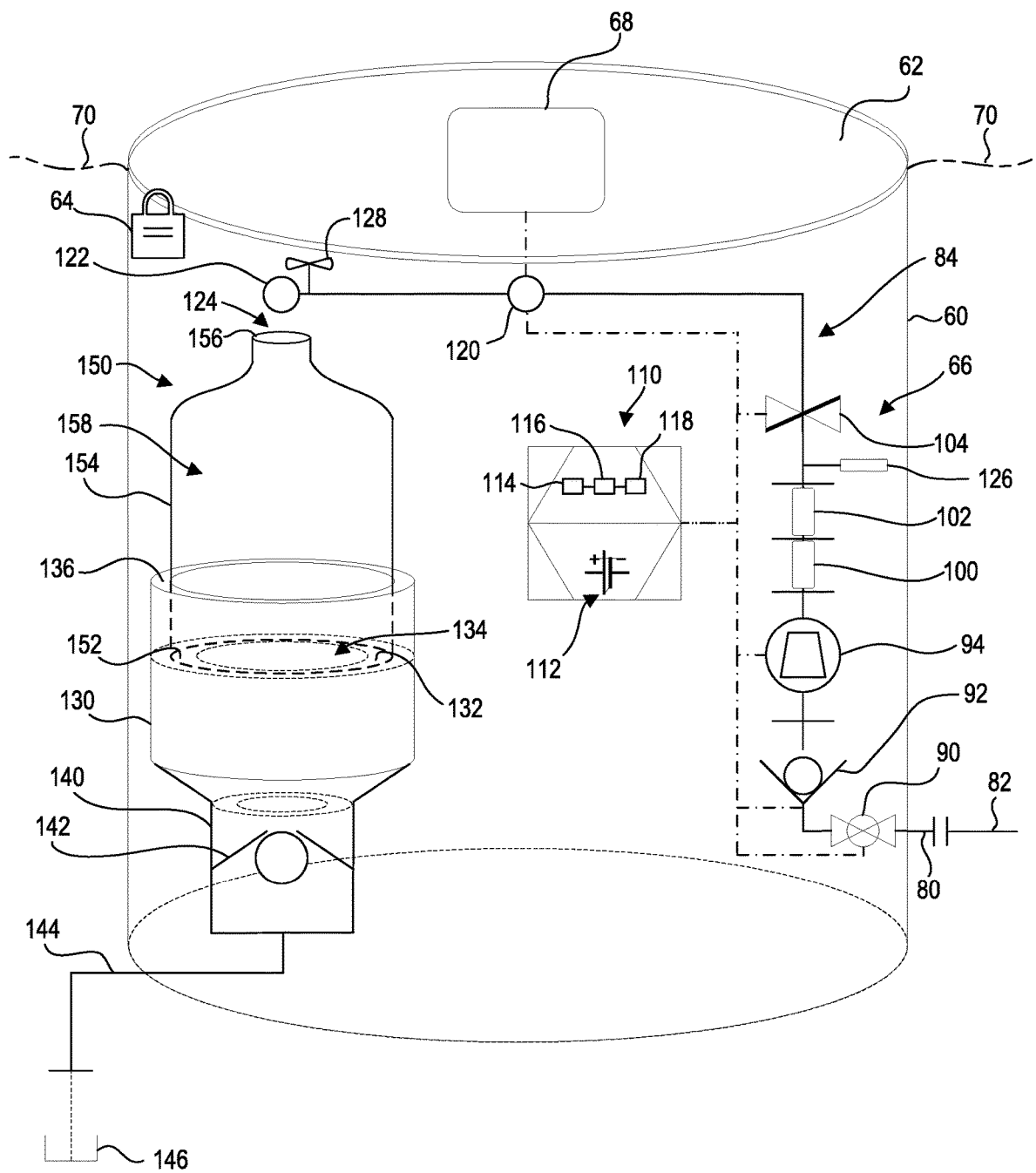
FIG. 2 is a schematic representation of a fluid sampling unit.

Referring to FIG. 2, a sampling unit 50 may include a housing 60. The housing 60 may be a cylindrical housing, polygonal housing, etc. In at least one approach, the housing 60 may be formed of polyvinyl chloride (PVC), high-density polyethylene (HDPE), or other polymers. In still other approaches, the housing 60 may be formed of metal or metal alloys (e.g. steel), concrete, or other suitable material.

The sampling unit 50 may include a cover 62. The cover 62 may have a shape and/or a dimension that matches or complements a corresponding dimension of the housing 60. For example, a generally circular cover may be provided to complement a generally cylindrical housing. As used herein, the term "generally cylindrical" refers to an elongated enclosure having a cross-section that is cylindrical, elliptical or polygonal, or is comprised of a combination of one or more straight sections and one or more arcs of constant radius or one or more arcs of varying radius.

The cover 62 may be formed of the same material as the housing 60, or may be formed of a different material. In at least one approach, the cover 62 may include an access port that may be, for example, an aperture or through-hole. The cover 62 may be releasably securable to the housing 60. For example, the cover 62 may be threadably securable to the housing 60. In this regard, one or both of the housing 60 and the cover 62 may be provided with one or more threads. In still another approach, the cover 62 may be secured to the housing 60 in via an interference fit interface. For example, a radially-outward surface of the cover 62 may be press-fit against a radially-inward surface of the housing 60. In at least one approach, the cover 62 may be securable to the housing 60 such that the cover 62 and the housing 60 form a fluid-tight (e.g., airtight and/or watertight) seal therebetween.

The sampling unit 50 may be sized such that it is a portable sampling unit. As used herein, a portable sampling unit may refer to a sampling unit that may be lifted by a human being or machine (e.g., a lift, a crane, a vehicle, etc.). In at least one approach, a portable sampling unit may be less than five feet in height, width (e.g., diameter), or both, and more preferably, less than three feet in height, width (e.g., diameter), or both, and more preferably, less than one foot in height, width (e.g., diameter), or both.

The sampling unit 50 may include a lock 64. The lock 64 may be used to restrict removal of the cover 62 from housing 60 to only those authorized to do so. For example, access may be limited to one or more of a public water system employee, a property owner, or a sampling unit 50 owner. The lock 64 may be a mechanically-actuated lock, an electronically-actuated lock, or combination thereof. For example, a mechanically-actuated lock may include a tubular lock, a cylindrical lock, an interconnected lock, a deadbolt lock, a mortise lock, a padlock, etc. An electronically-actuated lock may include an electromagnetic lock, an electronic strike, electronic deadbolts and latches, etc. The lock 64 may include one or more authentication interfaces. The authentication interface may be adapted to receive an authentication indication, for example, prior to actuating (e.g., unlocking) of the lock 64. The authentication indication may include one or more of numerical codes, passwords, passphrases, security tokens, biometrics, or wireless communications (e.g., radio-frequencies (RF), local area network communications such as IEEE 802.11 or Wi-Fi), Bluetooth, Zigbee, UWB, wireless USB, Z-Wave, or cellular communications such as GSM, WCDMA, LTE, CDMA2000).

The sampling unit 50 may include a user interface 68. The user interface 68 may be provided, for example, at the cover 62 (e.g., on a planar surface of the cover 62). In still another approach, the user interface 68 may be provided on the housing 60. In still another approach, the user interface may be remote from the housing 60 and the cover 62. The user interface 68 may be removably secured to the sampling unit 50, or may be rigidly secured to the sampling unit 50 such that the user interface 68 is not removable from the sampling unit 50.

The user interface 68 may include any suitable input and output devices. The input devices enable a user to input modifications or updates to information referenced by the various programs as described herein. The input devices may include, for instance, a control knob, an instrument panel, a keyboard, a scanner, a digital camera for image capture and/or visual command recognition, a touch screen, an audio input device (e.g., microphone), buttons, a mouse, or a touchpad. The output devices may include instrument cluster outputs (e.g., dials, lighting devices), actuators, a display (e.g., a liquid crystal display ("LCD"), a light emitting diode ("LED"), an organic light emitting diode ("OLED"), a flat panel display, a solid state display, a cathode ray tube ("CRT"), or a heads-up display), and speakers. The output devices may convey to a user, for example, a state or status of the sampling unit 50 or components of the sampling unit 50.

In at least one approach, the user interface 68 may include an override input for receiving a request or command to perform an override function. An override function may include, for example, effecting a particularly operation (e.g., a flushing or sampling operation) out of sequence or when not otherwise intended or expected.

In at least one approach, an output device may include one or more annunciation interfaces that may convey a sampling status. For example, a first visual indicator may be provided to indicate to a user that the sampling unit 50 is not in a user-sampling mode. The first visual indicator may be, for example, an LED that emits a first color such as red. A second visual indicator may be provided to indicate to a user that the sampling unit is in a user-sampling mode. The second visual indicator may be, for example, the same LED or a different LED that emits a second color such as green. In this way, a user may readily ascertain an operational status of the sampling unit 50 upon observation of the user interface 68.

In still another approach, the user interface 68 may be, or may include, a window formed of a transparent or translucent material. In this way, a user may visually observe internal components of the sampling unit 50 through the user interface 68. In still another approach, the user interface 68 may be, or may include, an access port. In this way, a user may access internal components of the sampling unit 50 through the user interface 68.

The housing 60, the cover 62, or cooperation of both the housing 60 and the cover 62 may define an interior cavity 66. The interior cavity 66 may be hollow or substantially hollow such that additional components may be received therein. In at least one approach, interior surfaces of the housing 60 may define a plurality (e.g., majority) of the internal surface area of the interior cavity 66. In this regard, the housing 60 may have a substantially U-shaped cross-section. In still another approach, interior surfaces of the cover 62 may define a plurality (e.g., majority) of the internal surface area of the interior cavity 66. In this regard, the cover 62 may have an inverted substantially U-shaped cross-section. In still other approaches, additional components may be provided that define a plurality (e.g., majority) of the internal surface area of the interior cavity 66.

The sampling unit 50 may be a submersible sampling unit. In this regard, one or both of the housing 60 and the cover 62 may be at least partially submersed within the ground, as indicated at ground 70. Submersing a sampling unit 50 into the ground 70 may be decrease the likelihood that one or more components of the sampling unit 50 may malfunction during freezing conditions. In still other approaches, such as where the sampling unit 50 is disposed in a temperature-regulated structure or located in a warm climate, the sampling unit 50 may be disposed substantially or entirely above ground.

In still another approach, the sampling unit 50 may be a standalone sampling unit that may be installed at or within a building. For example, the sampling unit 50 may be connected to a water line within a residential building or commercial building (e.g., under a sink or in a mechanical room). In one example approach, the sampling unit 50 may be installed similar to an under-counter reverse osmosis system, and may include a tap that dispenses into a sink or a drain. In such an approach, one or both of the housing 60 and the cover 62 may be omitted. Additional housing components may be provided to enclose one or more of the components discussed herein.

The sampling unit 50 may include a fluid inlet 80. The fluid inlet 80 may be fluidly connected to a fluid line or service line 82 at a first port, and may fluidly connect the service line 82 with an internal fluid line 84. The service line 82 may correspond to or may include, for example, a water main 32 that may be connected to a fluid source (e.g., a water tower 18), a service line 34 that may be connected to a water main 32), or an internal or external plumbing network that connects a building to a water main 32 or service line 34. In at least one approach, the fluid inlet 80 may be releasably connected to the service line 82. The fluid inlet 80 may include a connector hose that may extend through a wall of the sampling unit 50. The wall may be, for example, a sidewall of the housing 60, or a top wall of the cover 62.

A shutoff valve 90 may be provide proximate the fluid inlet 80. The shutoff valve 90 may be disposed within the interior cavity 66 of the sampling unit 50. In still another approach, the shutoff valve 90 may be disposed at the exterior of the sampling unit 50. In this way, the fluid inlet 80 may be disposed at an interior of the sampling unit 50, or may be omitted.

The shutoff valve 90 may be, for example, a ball valve. The shutoff valve 90 may be adapted to restrict or block a fluid flow from the fluid inlet 80 to the internal fluid line 84. In this way, an operator may close the shutoff valve 90 may be access components within the interior cavity 66 (e.g., for maintenance, repair, etc.) without having pressure from a service line 82. Closing the shutoff valve 90 may be a manual operation, or may be controlled by a control unit (e.g., control unit 110, discussed in greater detail elsewhere herein).

The sampling unit 50 may include a backflow preventer 92. The backflow preventer 92 may be, for example, a one-way valve such as a check valve. The backflow preventer 92 may be a self-automated valve that allows flow in one direction within the internal fluid line 84, and may automatically prevent back flow (reverse flow) when fluid in the internal fluid line 84 reverses direction; for example, during a low pressure event. As such the backflow preventer 92 may prevent any water, which may be copper- or lead-contaminated water, from backflowing into a distribution system (e.g., water distribution network 30 of FIG. 1).

The sampling unit 50 may include a turbine, such as microturbine 94. The microturbine 94 may include a compressor, combustor, turbine, and electric generator that may be disposed on one or more shafts. The microturbine 94 may be disposed within the sampling unit 50 such that the microturbine may harness fluid flowing through the internal fluid line 84. In this way, the microturbine 94 may generate electricity that may be used to power one or more components of the sampling unit 50, or that may be stored in a battery (e.g., battery 112, discussed in greater detail elsewhere herein). As such, the sampling unit 50 may be a self-powered sampling unit.

The sampling unit 50 may further include one or more plumbing lines, which may be metallic lines that include lead and/or copper. The plumbing lines may include a first metallic line that includes lead, such as lead line 100, shown in FIG. 2. The plumbing lines may also, or may instead, include a second metallic line that includes copper, such as copper line 102. The plumbing lines may be disposed within the fluid path of the internal fluid line 84, and may take any suitable shape, such as pipes, fittings, nipples, coils, plates, etc.

The plumbing lines may generally correspond to plumbing lines provided in a water distribution system (e.g., water distribution network 30 of FIG. 1). As such, a first plumbing line, lead line 100, may have lead content. The lead line 100 may be, for example, a primarily brass plumbing line having lead content. A second plumbing line may be provided that is composed of material different than the first plumbing line. The second plumbing line may be the copper line 102 having copper content. The lead content and the copper content may be included on internal surfaces of the lead line 100 and copper line 102, respectively. As such, water flowing through the internal fluid line 84 may be exposed the lead content and/or the copper content.

The lead line 100 and the copper line 102 may be provided in series. In at least one approach, the lead line 100 may be disposed upstream from the copper line 102 such that water provided through the fluid inlet 80 enters the lead line 100 prior to entering the copper line 102. In still another approach, the copper line 102 may be disposed upstream from the lead line 100 such that water provided through the fluid inlet 80 enters the copper line 102 prior to entering the lead line 100. The copper line 102 may be arranged immediately adjacent to the lead line 100 such that water exiting the lead line 100 is directly provided to the copper line 102, or vice versa. In still another approach, an additional line or component of the sampling unit 50 may be provided between the lead line 100 and the copper line 102 such that the lead line 100 and the copper line 102 are not immediately adjacent. One or both of the lead line 100 and the copper line 102 may be provided upstream of at least one (and preferably both) of the backflow preventer 92 and the microturbine 94.

The sampling unit 50 may include an electrically-actuated (e.g., electromechanical or electropneumatic) valve that may be adapted to control fluid flow through at least a portion the internal fluid line 84 of the sampling unit 50. For example, a solenoid valve 104 may be provided to control fluid flow within the sampling unit 50. In at least one approach, when the solenoid valve 104 is in an open condition, fluid may be permitted to flow from one or more plumbing lines (e.g., lead line 100 and/or copper line 102) through downstream portions of the internal fluid line 84. When the solenoid valve 104 is in a closed condition, fluid may be permitted to flow from one or more plumbing lines (e.g., lead line 100 and/or copper line 102) through downstream portions of the internal fluid line 84.

As used herein, the terms "downstream" and "upstream" refer to the flow of fluid through the sampling unit 50. A first component is "upstream" from a second component if a fluid flow communicates with the first component prior to communicating with the second component. Conversely, a first component is "downstream" from a second component if a fluid flow communicates with the second component prior to communicating with the first component. The phrases "downstream fluid communication" and "upstream fluid communication" refer to both the fluid communication of two or more components and the relative positioning along the fluid flow of the two or more components.

In at least one approach, the sampling unit 50 may be provided with a control device such as a water hammer arrestor 126. The water hammer arrestor 126 may include, for example, a sliding piston that may absorb sudden pressure changes in the internal fluid line 84. The water hammer arrestor 126 may be provided upstream from the solenoid valve 104 such that the water hammer arrestor 126 may act on a fluid flow that has been inhibited by the solenoid valve 104. For example, the water hammer arrestor 126 may be disposed upstream from the solenoid valve 104 and downstream from one or both of the lead and copper lines 100, 102. In still another example, the water hammer arrestor 126 may be disposed upstream from the solenoid valve 104 and both of the copper and lead lines 100, 102. Other control devices for absorb sudden pressure changes in the internal fluid line 84 are expressly contemplated for use in place of, or in addition to, the water hammer arrestor 126.

Operation of the solenoid valve 104 may be controlled by control unit 110. The control unit 110 may include, or may be electrically coupled to, a battery 112. Although depicted as a component of the control unit 110, the battery 112 may instead be disposed remote from the control unit 110. The battery 112 may be a rechargeable battery that may be in electrical communication with the microturbine 94. In this way, the battery 112 may receive and store electricity generated by the microturbine 94, and may further provide electricity to power one or more components of the sampling unit 50, such as the user interface 68, the solenoid valve 104, the control unit 110, etc.

In still another approach, the battery 112 may receive and store electricity provided by other power sources, such as one or both of a wind turbine and a photovoltaic system (which may include one or more solar panels). Other sources of energy, including marine energy, hydroelectric, and geothermal energy, are expressly contemplated for supplying energy to the battery.

In still another approach, one or more components of the sampling unit 50 may be directly connected to an external source of power (e.g., grid or mains power). As such, the solenoid valve 104 may be powered by the external source of power. In this way, the battery 112 may serve as a backup source of power, or may be omitted from the sampling unit.

The control unit 110 may further include one or more of a processor or controller 114, a memory 116, and a communication device 118. The processor or controller 114 may be any suitable processing device or set of processing devices such as, but not limited to: a microprocessor, a microcontroller-based platform, a suitable integrated circuit, or one or more application-specific integrated circuits (ASICs).

The memory 116 may be a computer readable medium on which one or more sets of instructions, such as the software for operating the methods of the present disclosure can be embedded. The instructions may embody one or more of the methods or logic as described herein. In at least one approach, the instructions may reside completely, or at least partially, within any one or more of the memory 116, the computer readable medium, and/or within the controller 114 during execution of the instructions.

The memory 116 may be volatile memory (e.g., RAM, which can include non-volatile RAM, magnetic RAM, ferroelectric RAM, and any other suitable forms); non-volatile memory (e.g., disk memory, FLASH memory, EPROMs, EEPROMs, memristor-based non-volatile solid-state memory, etc.); unalterable memory (e.g., EPROMs); read-only memory; a hard drive; a solid state hard drive; or a physical disk such as a DVD. In at least one approach, the memory 116 includes multiple kinds of memory, particularly volatile memory and non-volatile memory.

The terms "non-transitory computer-readable medium" and "computer-readable medium" should be understood to include a single medium or multiple media, such as a centralized or distributed database, and/or associated caches and servers that store one or more sets of instructions. The terms "non-transitory computer-readable medium" and "computer-readable medium" also include any tangible medium that is capable of storing, encoding or carrying a set of instructions for execution by a processor, or that cause a system to perform any one or more of the methods or operations disclosed herein. As used herein, the term "computer readable medium" is expressly defined to include any type of computer readable storage device and/or storage disk.

The communication device 118 may include a wired or wireless network interface to enable communication with an external network. As such, the communication device 118 may be a wireless communication interface that includes a transmitter, a receiver, or a transceiver.

The external network may be a collection of one or more networks, including standards-based networks (e.g., 2G, 3G, 4G, Universal Mobile Telecommunications Autonomous valet parking system (UMTS), GSM® Association, Long Term Evolution (LTE)™, or more); WiMAX; Bluetooth; near field communication (NFC); WiFi (including 802.11 a/b/g/n/ac or others); WiGig; Global Positioning System (GPS) networks, etc. Further, the external network(s) may be a public network, such as the Internet; a private network, such as an intranet; or combinations thereof, and may utilize a variety of networking protocols now available or later developed including, but not limited to, TCP/IP-based networking protocols. The communication device 118 may also include a wired or wireless interface to enable direct communication with an electronic device, such as a USB or Bluetooth interface.

In this way, the communication device 118 may enable external control (e.g., remote control) of one or more components or operations of the sampling unit 50. External control may be provided through one or more external interfaces (e.g., web browser, dedicated application, etc.) that may be provided at one or more external devices (e.g., computer system configurations, including personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, various storage devices, and the like).

In at least one approach, one or more components of the control unit 110, such as the battery 112, the controller 114, the memory 116, and the communication device 118, may be disposed within the interior cavity 66 of the sampling unit 50. In still another approach, one or more components of the control unit 110, such as the battery 112, the controller 114, the memory 116, and the communication device 118, may be disposed at an exterior of the sampling unit 50. Exterior components may communicate with interior components through wired protocols, wireless protocols, or a combination of wired and wireless protocols. For example, a controller may be disposed at an exterior of the sampling unit 50, and may wirelessly effect actuation of an internal actuator to control the solenoid valve 104.

The sampling unit 50 may include a flow meter, such as water meter 120. The water meter 120 may be disposed within the internal fluid line 84, and may be adapted to measure one or more parameters (such as volume, displacement, flow rate, etc.) of the fluid passing through the internal fluid line 84. The water meter 120 may be a mechanical or non-mechanical (e.g., electromagnetic or ultrasonic) water meter. The water meter 120 may be in communication with one or more components of the sampling unit 50. For example, the water meter 120 may receive power from the battery 112. The water meter 120 may also be in communication with other components of the control unit 110, such as the controller 114 (e.g., to report a status of the water meter 120 or sampling unit 50), the memory 116 (e.g., to store a status of the water meter 120 or sampling unit 50), and the communication device 118 (e.g., to externally communicate a status of the water meter 120 or sampling unit 50). The water meter 120 may include an analog or digital display. If the user interface 68 is, or includes, a window, the display may be provided proximate the user interface 68 such that a user may visually observe the display through the user interface 68.

The sampling unit 50 may include a dispenser 122. The dispenser may be, for example, a sample tap. The dispenser 122 may be disposed within the internal fluid line 84 such that fluid passing through the solenoid valve 104 pass through the dispenser 122. Fluid passing through the dispenser 122 may fall vertically through an air gap 124 provided between the dispenser 122 and a receptacle basin 130 disposed vertically (e.g., gravitationally) below the dispenser 122.

In still other approaches, the dispenser 122 may be an elongate sample tap, a flexible sample tap, or a telescoping sample tap. In this way, at least a portion of the dispenser may be removed or lifted from the interior cavity 66 of the sampling unit 50.

In at least one approach, the sampling unit 50 may be provided with a valve that may be a flow control valve 128. The flow control valve 128 may be at or proximate (e.g., upstream from) the dispenser 122. The flow control valve 128 may be adapted to reduce a fluid flow through the dispenser 122. For example, the flow control valve 128 may be a ball valve adapted to at least partially block fluid flow through the valve to reduce the volumetric flow rate of fluid through the flow control valve 128, and thereby reduce the volumetric flow rate of fluid through the dispenser 122. In this way, an operator may collect a sample of fluid from the dispenser 122 in a controlled manner, controlled at least partially at the flow control valve 128, as discussed in greater elsewhere herein.

The receptacle basin 130 may include a floor 132 that defines an aperture 134, and a cylindrical wall 136 that extends axially from the floor 132 and annularly about the aperture 134. An internal drain 140 may extend from the receptacle basin 130. As such, fluid passing through the aperture 134 may be directed through the internal drain 140. In at least one approach, a check valve 142 may be provided; for example, within the internal drain 140. Similar to backflow preventer 92, the check valve 142 may be a self-automated valve that allows flow in one direction within the internal fluid line 84, and may automatically prevent back flow (reverse flow) into the receptacle basin 130.

The internal drain 140 may be in fluid communication with a fluid outlet 144. The fluid outlet 144 may include a connector hose that may extend through a wall of the sampling unit 50. The wall may be, for example, a sidewall of the housing 60, or a top wall of the cover 62. The fluid outlet 144 may direct fluid to an external drain 146. The fluid directed to the external drain 146 may be referred to as wastewater. In at least one approach, the external drain 146 may drain the wastewater to a sewer or sewer system, which may direct the wastewater to a municipal wastewater system, to a watershed or surface water, to the environment, or to other known wastewater destinations.

The sampling unit 50 may include, or may receive, a sample receptacle 150. The sample receptacle 150 may be, for example, a bottle, canister, cartridge, jar, case, or other suitable container adapted to receive and maintain a fluid. The sample receptacle 150 may be a removable receptacle that may be removably disposed within a flow path of the internal fluid line 84. In at least one approach, the sample receptacle 150 may be disposed at least partially within the receptacle basin 130. For example, a base 152 of the sample receptacle 150 may be disposed on the floor 132, and walls 154 of the sample receptacle 150 may extend at least partially within the cylindrical wall 136. A port 156 of the sample receptacle 150 may be disposed vertically (e.g., gravitationally) below the dispenser 122 such that fluid flowing from the dispenser 122 is received within an internal compartment 158 of the receptacle 150.

Components of the sampling unit 50 may be adapted to simulate a service line to a service location. Furthermore, the sampling unit 50 may be operated to simulate a water sampling protocol that may correspond to sampling protocols often trusted to be performed by volunteer residents.

Figure 3:
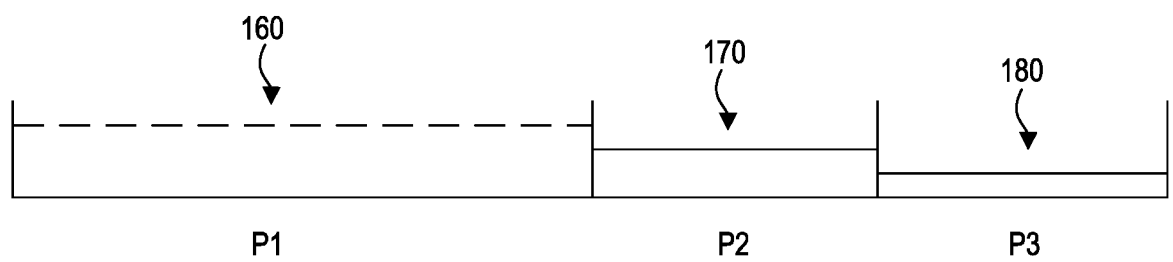
FIG. 3 is a schematic representation of various operational modes of the fluid sampling unit.

Referring now to FIG. 3, the sampling unit 50 may be adapted (e.g., via a controller) to operate in one or more operational modes. For example, the sampling unit 50 may operate a first operational mode 160, a second operational mode 170, and a third operational mode 180. Although three operational modes are described in detail herein, it is expressly contemplated that one operational, two operational modes, four operational modes, or five or more operational modes may be operated at the sampling unit 50.

In the first operational mode, fluid may be drawn from a fluid source (e.g., service line 82) and into the sampling unit (e.g., through an inlet valve such as shutoff valve 90). Fluid drawn into the sampling unit 50 may traverse through at least a portion of internal fluid line (e.g., internal fluid line 84) of the sampling unit. For example, fluid may flow from the service line to flow through one or more of a backflow preventer (e.g., backflow preventer 92), a turbine (e.g., microturbine 94), a lead line (e.g., lead line 100), and a copper line (e.g., copper line 102).

While the sampling unit 50 is in the first operational mode 160, a valve (e.g., solenoid valve 104) may be selectively opened and closed. For example, the valve may be programmed or controlled to close for a hold time (e.g., 30 seconds, 1 minute, 5 minutes, 10 minutes, 30 minutes, 1 hour, 2 hours, etc.) The hold time may be a predetermined constant hold time, multiple predetermined variable hold times, or randomly selected hold times. As used herein, a predetermined time may be a programmed time. The programmed time may be stored in a memory, such as memory 116. The hold time may be a programmed hold time that may be fixed (e.g., unalterable), or may be alterable (e.g., alterable by an end user after an initial programming). The hold time may be programmed or altered, for example, at the user interface 68 of the sampling unit 50, or at an external device (e.g., remote computer or nomadic device) that is in communication with the sampling unit 50 (e.g., through the communication device 118).

While the valve is closed, at least a portion of the fluid received in the fluid line is maintained within the lead and copper lines.

Upon expiration of the hold time, the valve may be opened and fluid that was previously maintained within the lead and copper lines is driven (e.g., under pressure from the service line) through the internal fluid line 84 to the dispenser 122.

In this first operational mode, no sampling receptacle may be provided in the receptacle basin 130. As such, fluid passed through the dispenser 122 may fall (e.g., vertically or substantially vertically) through the air gap 124, and through the aperture 134 in the floor 132 of the receptacle basin 130. The fluid may then be directed to the fluid outlet 144 and to the external drain 146. From the external drain 146, the fluid may be discharged as wastewater, as discussed in greater detail elsewhere herein.

In this way, while in the first operational mode, the sampling unit 50 may repeatedly hold and discharge fluid. The repeated hold-discharge operation may be programmed to simulate a consumer usage of fluid received from a fluid source (e.g., a service line of a public water distribution network). For example, the sampling unit 50 may be programmed to simulate water consumption patterns of a typical residential consumer. In at least one approach, the sampling unit 50 may consume and discharge approximately 10-15 gallons per hour. The first operational mode may be referred to as a regular, normal, or simulation mode of operation.

The sampling unit 50 may be maintained in the first operational mode for a first predetermined period of time, indicated as P1 on in FIG. 3. The first predetermined period of time P1 may be, for example, approximately 12 hours. The first predetermined period of time P1 may be set and/or varied through any of the approaches discussed herein. As discussed, one or more indicators may be provided at the sampling unit 50 (or remote from the sampling unit 50) to indicate to a user that the sampling unit 50 is operating the first operational mode 160.

Upon expiration of the first predetermined period of time P1, the sampling unit 50 may be programmed to operate in a second operational mode 170. In the second operational mode 170, the sampling unit 50 (e.g., via the control unit 110) may be adapted to close a valve, such as the solenoid valve 104. The solenoid valve 104 may be closed for a second predetermined period of time P2. During the second predetermined period of time P2, at least a portion of the fluid received in the fluid line is maintained within the lead and copper lines. As such, the second operational mode 170 may be referred to as a stagnation mode.

The second predetermined period of time P2 may be selected from a time period in the range, for example, of approximately 2 hours to approximately 12 hours. For example, the second predetermined period of time P2 may be approximately 6 hours. In at least one approach, the second predetermined period of time P2 may be selected to generally correspond to a minimum stagnation time as established by local, state, or federal water sampling regulations. As with the first predetermined period of time P2, the second predetermined period of time P2 may be set and/or varied through any of the approaches discussed herein. As discussed, one or more indicators may be provided at the sampling unit 50 (or remote from the sampling unit 50) to indicate to a user that the sampling unit 50 is operating the second operational mode 170.

In at least one approach, the sampling unit 50 may be adapted to operate in the second operational mode 170 immediately subsequent to the operation in the first operational mode 160. In still another approach, the sampling unit 50 may operate in one or more intermediary modes prior to entering the second operational mode 170.

Upon expiration of the second predetermined period of time P2, the sampling unit 50 may further be adapted (e.g., via a controller) to operate in a third operational mode 180. During the third operational mode 180, fluid that was maintained in the lead and copper lines 100, 102 may be collected for sampling.

More particularly, during the third operational mode 180, the solenoid valve 104 is initially maintained in the closed position. An operator may place a sample receptacle 150 below the dispenser 122; for example, within the receptacle basin 130. In this way, the sample receptacle 150 may be positioned to receive fluid to be dispensed from the dispenser 122.

With the sample receptacle 150 in place, the operator may initiate opening of the solenoid valve 104. This may be performed at the solenoid valve 104 (e.g., via a push-button at the solenoid valve 104), at the user interface 68, or at an external device in communication with the sampling unit 50 (e.g., via the communication device 118 of the control unit 110).

Upon opening of the solenoid valve 104 during the third operational mode 180, fluid that has been maintained in the lead and copper lines 100, 102 may be directed through the dispenser 122 and into the sample receptacle 150. As discussed, a flow control valve 128 may be provided to enable operator control over the volumetric flow rate through the dispenser 122.

The operator may maintain the sample receptacle 150 below the dispenser 122 until a desired or predetermined volume of fluid is received in the sample receptacle 150. Upon removal of the sample receptacle 150, excess fluid flowing during the third operational mode 180 may be directed through the aperture 134 in the floor 132 of the receptacle basin 130, to the fluid outlet 144, and to the external drain 146. From the external drain 146, the fluid may be discharged as wastewater, as discussed in greater detail elsewhere herein.

The sampling unit 50 may operate in the third operational mode 180 or a third predetermined period of time P3. The third predetermined period of time P3 may be set and/or varied through any of the approaches discussed herein. The third predetermined period of time P3 may be selected such that the sum of the second predetermined period of time P2 and the third predetermined period of time P3, which may be referred to as a total stagnation time, does not exceed a predetermined maximum stagnation time. The predetermined maximum stagnation time may generally correspond to a maximum stagnation time as established by local, state, or federal water sampling regulations. For example, if a required stagnation period is in the range of a minimum of six hours and a maximum of 12 hours, the second predetermined period of time P2 may be programmed as 6 hours, and the third predetermined period of time P3 may also be programmed as 6 hours. In this way, the total operation in the first and second operational modes (total stagnation time) does not exceed the maximum stagnation time of 12 hours.

As discussed, one or more indicators may be provided at the sampling unit 50 (or remote from the sampling unit 50) to indicate to a user that the sampling unit 50 is operating the third operational mode 180. In this way, a user may be informed of the availability of fluid ready for sampling.

In at least one approach, the sampling unit 50 may be adapted to operate in the third operational mode 180 immediately subsequent to the operation in the second operational mode 170. In still another approach, the sampling unit 50 may operate in one or more intermediary modes prior to entering the third operational mode 180.

During the third operational mode 180, a user may command a sample of fluid previously maintained in the lead and copper lines during the second operational mode 170. The sample fluid may be collected in a removable sample receptacle 150. Upon removable of the sample receptacle from the sampling unit, the sample fluid collected in the sample receptacle may be tested; for example, for lead and/or copper content. Lead or copper content at or above predetermined levels (also known as action levels) may indicate corrosion of the lead or copper lines, respectively. An action level for lead may be, for example, 0.015 milligrams per liter (mg/L). An action level for copper may be, for example, 1.3 mg/L. Lead or copper content at or above predetermined levels may trigger requirements for a public water system to minimize exposure to lead and copper in drinking water (e.g., water quality parameter monitoring, corrosion control treatment, source water monitoring/treatment, public education, and lead service line replacement.)

In addition to lead and copper, other additional parameters may be tested and observed from the sampled water. For examples, water quality parameters such as acidity (pH), alkalinity, biological oxygen demand (BOD), carbonaceous biochemical oxygen demand (CBOD), chemical oxygen demand (COD), conductivity, dissolved oxygen (DO), pathogenic or disease-causing bacteria and viruses (e.g., fecal coliform, enterococci, and *E. coli* bacteria), hardness, metal concentrations, salinity, turbidity, nutrients (e.g., total nitrogen (TN) and total phosphorus (TP)), chlorine, and chlorophyll may be tested.

Upon expiration of the third predetermined period of time P3, the sampling unit 50 may be adapted to return to operation in the first operational mode 160. In at least one approach, the sampling unit 50 may be adapted to operate in the first operational mode 160 immediately subsequent to the operation in the third operational mode 180. In still another approach, the sampling unit 50 may operate in one or more intermediary modes prior to entering the first operational mode 160.

Figure 4:
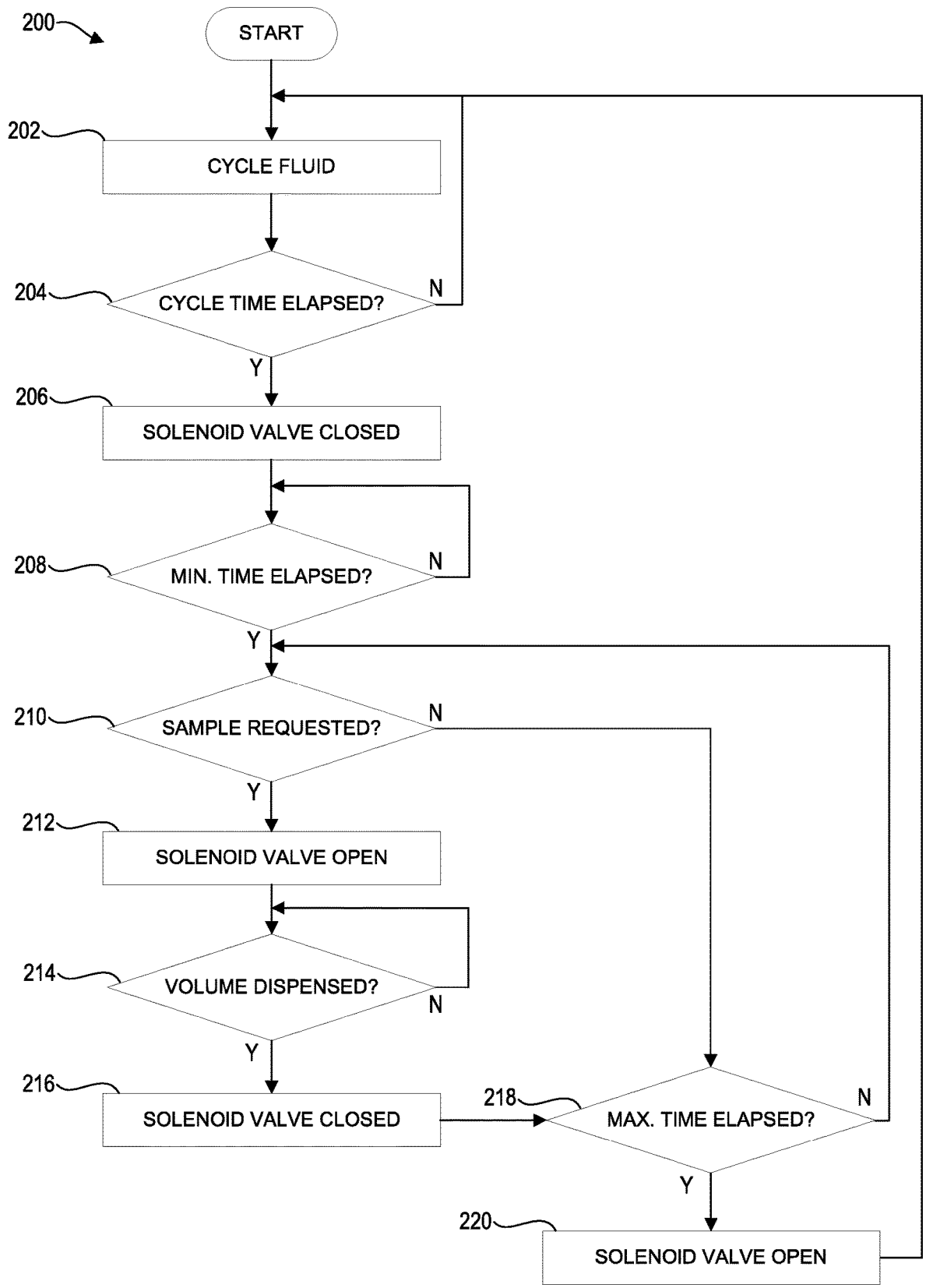
FIG. 4 is a flow chart depicting an example approach for a fluid sampling unit.

Referring now to FIG. 4, a method 200 of operating a sampling unit (e.g., sampling unit 50) is provided. The method may include cycling 202 fluid into and out of the sampling unit 50. The cycling performed at step 202 may generally correspond to the first operational mode 160 discussed herein. During step 202, an inlet valve (e.g., shutoff valve 90) is in an open configuration to permit fluid flow from a fluid source (e.g., service line 82) and into at least a portion of internal fluid line (e.g., internal fluid line 84) of the sampling unit. Also during step 202, the solenoid valve may be selectively opened and closed to permit and prohibit fluid flow from the fluid source, through the dispenser 122, and to the external drain 146.

At step 204, a determination may be made (e.g., at or via the control unit 110) as to whether a cycle time has elapsed. The cycle time may generally correspond to the first predetermined period of time P1 discussed with respect to FIG. 3.

If the cycle time has elapsed, the method continues to step 206, where the solenoid valve is actuated to, or maintained in, the closed position. Step 206 may generally correspond to the second operational mode 170 discussed herein.

At step 208, a determination may be made (e.g., at or via the control unit 110) as to whether a minimum stagnation time has elapsed. The minimum stagnation time may generally correspond to the second predetermined period of time P2 discussed with respect to FIG. 3. As discussed, the sampling unit may be operated to simulate a water sampling protocol. In this regard, at least some of the fluid received in the internal fluid line may be maintained in the lead line and/or the copper line for the second predetermined period of time. For example, to simulate water sampling protocols, the fluid may be maintained in the lead line and/or the copper line for a time period in the ranges of 1 hour to 48 hours, 2 hours to 24 hours, 4 hours to 16 hours, or 6 hours to 12 hours. In at least one approach, the fluid may be maintained in the lead line and/or the copper line for at least 1 hour, 2 hours, 4 hours, and preferably at least 6 hours.

Optionally, step 208 may include an override determination. For example, if an override request is received while the minimum stagnation time has not yet elapsed, the method may include opening the solenoid valve. An override request may be received at additional steps during the operation of the sampling unit. As such, it is expressly contemplated that an override request may be received, and the sampling unit may perform an override function, at various operational stages discussed herein.

If the minimum stagnation time has elapsed, the method continues to step 210, where a determination may be made (e.g., at or via the control unit 110) as to whether a sample has been requested. A sample may requested, for example, by an operator. As discussed, the request may be performed at the solenoid valve 104 (e.g., via a push-button at the solenoid valve 104), at the user interface 68, or at an external device in communication with the sampling unit 50 (e.g., via the communication device 118 of the control unit 110). In at least one approach, prior to requesting a sample (or shortly thereafter), the method may include the step of receiving a sample receptacle 150 proximate the dispenser 122 to receive fluid discharged from the dispenser 122. In at least one approach, one or more sensors (e.g., weight sensor, light sensor, etc.) may be provided to detect the presence of a sample receptacle.

If a sample request has not been received at step 210, the method continues to step 218, discussed in greater detail below.

If a sample request is received at step 210, the method continues to step 212, where the solenoid valve is opened. Opening of the solenoid valve discharges fluid previously maintained in the lead and copper lines through the dispenser 122. At least a portion of the discharged fluid may be received within the sample receptacle 150 for subsequent sampling.

From step 212, the method proceeds to step 214, where a determination may be made (e.g., at or via the control unit 110) as to whether a commanded volume of fluid has been discharged. In at least one approach, an indication of the commanded volume of fluid may be a manual "stop" input provided by an operator, and may be provided in a manner similar to the sample request indicated at step 210 (e.g., a command provided at or communicated to the control unit 110). In still another approach, the commanded volume of fluid is a predetermined volume of discharged fluid. Such a determination may be made based at least in part on information received from the water meter 120. The predetermined volume of fluid may be a programmed parameter, and may be set and/or varied through any of the approaches discussed herein.

In response to determining the commanded volume of fluid has been dispensed, the method may proceed to step 216, where the solenoid valve is closed.

From step 216, the method proceeds to step 218, where a determination may be made (e.g., at or via the control unit 110) as to whether a maximum stagnation time has elapsed. The maximum stagnation time may generally correspond to the third predetermined period of time P3 discussed with respect to FIG. 3.

If it is determined at step 218 that the maximum stagnation time has not elapsed, the method returns to step 210, where the controller monitors for a sample request and expiration of the maximum stagnation time.

If it is determined at step 218 that the maximum stagnation time has elapsed, the method continues to step 220, where the solenoid valve is opened. This step may be referred to as a flushing step, as water that has been maintained within the lead and copper lines for the maximum stagnation time is discharged to the drain.

After step 220, the method may return to step 202, where the sampling device repeats a cycling process.

In at least one approach, an external database or log may be compiled as a function of operation of one or more sampling units 50. For example, an individual sampling unit 50 may communicate (e.g., via a communication device 118) a status, a change in status, or other operational parameters of the sampling unit 50. In this way, a municipality, for example, may observe the operation of one or more sampling units to ensure compliant sampling procedures were followed in the collection of a given water sample. A first sampling unit may be provided with a unique identifier that distinguishes the first sampling unit from a second sampling unit, also having a unique identifier. As such, a municipality may be provided with greater transparency or control over the sampling procedures performed.

As such, the sampling unit and methods of operation discussed herein provide for automated sampling of water in a public water distribution network. Repeatability and reliability are thereby increased as compared to traditional volunteer sampling operations.

While exemplary embodiments are described above, it is not intended that these embodiments describe all possible forms encompassed by the claims. The words used in the specification are words of description rather than limitation, and it is understood that various changes may be made without departing from the spirit and scope of the disclosure. As previously described, the features of various embodiments may be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics may be compromised to achieve desired overall system attributes, which depend on the specific application and implementation. These attributes may include, but are not limited to cost, strength, durability, life cycle cost, marketability, appearance, packaging, size, serviceability, weight, manufacturability, ease of assembly, etc. As such, embodiments described as less desirable than other embodiments or prior art implementations with respect to one or more characteristics are not outside the scope of the disclosure and may be desirable for particular applications.

What is claimed is:

1. A fluid sampling unit comprising:
   a housing;
   a shutoff valve adapted to selectively permit and restrict fluid flow to a fluid line disposed within an internal cavity of the housing;
   an electrically-actuated valve disposed within the housing downstream from, and in fluid communication with, the shutoff valve;
   a first metallic line including copper in fluid communication with and between the shutoff valve and the electrically-actuated valve;
   a second metallic line including lead in fluid communication with and between the shutoff valve and the electrically-actuated valve; and a control unit including a controller adapted to selectively actuate the electrically-actuated valve to at least partially open the electrically-actuated valve in response to the fluid flow being maintained within the first and second metallic lines for a programmed period of time.

2. The fluid sampling unit of claim 1, wherein the programmed period of time is at least six hours.

3. The fluid sampling unit of claim 1, further comprising a removable cover securable to the housing to selectively permit and restrict access to the internal cavity of the housing.

4. The fluid sampling unit of claim 1, further comprising at least one additional line formed of metal or plastic in fluid communication with and between the shutoff valve and the electrically-actuated valve.

5. The fluid sampling unit of claim 1, further comprising:
a flow meter disposed within the housing and in fluid communication with the electrically-actuated valve, wherein the controller is adapted to selectively actuate the electrically-actuated valve to at least partially close the electrically-actuated valve in response to a predetermined volume of the fluid flow flowing through the flow meter.

6. The fluid sampling unit of claim 1, further comprising:
a communication device including a communication interface adapted to receive, send, or both receive and send wireless communications.

7. The fluid sampling unit of claim 1, further comprising:
a backflow preventer disposed fluidly between the shutoff valve and the electrically-actuated valve to prevent backflow of the fluid flow through the shutoff valve.

8. The fluid sampling unit of claim 1, further comprising:
a turbine disposed within the housing in fluid communication with and between the shutoff valve and the electrically-actuated valve; and
a battery in electrical communication with the turbine.

9. The fluid sampling unit of claim 8, wherein the battery is in electrical communication with the electrically-actuated valve.

10. The fluid sampling unit of claim 1, further comprising:
a dispenser disposed within the housing downstream from the electrically-actuated valve; and
a receptacle basin disposed within the housing and gravitationally below the dispenser to receive the fluid flow from the dispenser.

11. The fluid sampling unit of claim 10, wherein the dispenser is spaced vertically above the receptacle basin such that the sampling unit defines an airgap between the dispenser and the receptacle basin.

12. The fluid sampling unit of claim 10, further comprising:
a sample receptacle removably received within the receptacle basin to receive the fluid flow from the dispenser.

13. The fluid sampling unit of claim 10, further comprising:
a fluid outlet in fluid communication with the receptacle basin; and
a check valve fluidly disposed between the receptacle basin and the fluid outlet.

14. A method for sampling fluid, comprising:
fluidly connecting a fluid sampling unit to a service line of a public water system that includes a plurality of service lines, the fluid sampling unit including a housing having an electrically-actuated valve, a first metallic line including copper, and a second metallic line including lead disposed within an internal cavity of the housing;
via a controller,
successively opening and closing the electrically-actuated valve for a first programmed period of time;
subsequent to expiration of the first programmed period of time, maintaining the electrically-actuated valve in a closed configuration for a second programmed period of time to maintain a fluid volume within the first and second metallic lines; and
subsequent to expiration of the second programmed period of time and during a third programmed period of time, at least partially opening the electrically-actuated valve responsive to a sampling request to discharge the fluid volume.

15. The method of claim 14, wherein the second programmed period of time is at least six hours.

16. The method of claim 14, wherein the fluid sampling unit is a portable, self-contained fluid sampling unit.

17. The method of claim 14, wherein at least partially opening the electrically-actuated valve during the third programmed period of time communicates the fluid volume to a removable sample receptacle disposed within the internal cavity of the housing.

18. The method of claim 17, further comprising:
via the controller, at least partially opening the electrically-actuated valve responsive to an expiration of the third programmed period of time.

19. The method of claim 18, further comprising:
removing a cover that is removably secured the housing; and
removing the removable sample receptacle, including a fluid sample within the removable sample receptacle, from the housing.

20. The method of claim 19, further comprising:
sampling the fluid sample to determine at least one of a lead content level and a copper content level within the fluid sample.

* * * * *